US009127261B2

(12) United States Patent
Neubauer et al.

(10) Patent No.: US 9,127,261 B2
(45) Date of Patent: Sep. 8, 2015

(54) ENZYME-BASED FED-BATCH TECHNIQUE IN LIQUID CULTURES

(75) Inventors: Peter Neubauer, Berlin (DE); Antje Neubauer, Berlin (DE); Antti Vasala, Oulu (FI)

(73) Assignee: BioSilta Oy, Oulu (FI)

( * ) Notice: Subject to any disclaimer, the term of this patent is extended or adjusted under 35 U.S.C. 154(b) by 0 days.

(21) Appl. No.: 13/201,869

(22) PCT Filed: Mar. 4, 2010

(86) PCT No.: PCT/EP2010/052780
§ 371 (c)(1),
(2), (4) Date: Oct. 24, 2011

(87) PCT Pub. No.: WO2010/100239
PCT Pub. Date: Sep. 10, 2010

(65) Prior Publication Data
US 2012/0045836 A1   Feb. 23, 2012

(30) Foreign Application Priority Data

Mar. 5, 2009   (EP) .................................... 09154440

(51) Int. Cl.
C12N 1/10      (2006.01)
C12N 5/071     (2010.01)
C12N 1/20      (2006.01)
C12N 1/00      (2006.01)
C12N 5/04      (2006.01)
C12N 1/14      (2006.01)
C12N 1/22      (2006.01)
C12P 21/02     (2006.01)

(52) U.S. Cl.
CPC .. *C12N 1/22* (2013.01); *C12P 21/02* (2013.01)

(58) Field of Classification Search
CPC .................................. C12N 1/22; C12P 21/02
See application file for complete search history.

(56) References Cited

U.S. PATENT DOCUMENTS 3,926,723 A      12/1975 Green et al.
6,190,913 B1 *    2/2001 Singh ........................... 435/394
7,320,884 B2      1/2008 Anderson et al.
2006/0211101 A1*  9/2006 Chotani et al. ............. 435/136
2010/0099164 A1*  4/2010 Vasala et al. ................ 435/243
2011/0244573 A1* 10/2011 Neubauer et al. .......... 435/404

FOREIGN PATENT DOCUMENTS

JP       06-291741 A       10/1994
WO       01/25467 A1        4/2001
WO       03/066826          8/2003
WO       2007/060235 A1     5/2007
WO       2008/065254 A1     6/2008
WO    WO 2008/065254    *   6/2008    ............... C12N 1/04
WO       2009/025547 A1     2/2009

OTHER PUBLICATIONS

Panula-Perala et al., Enzyme controlled glucose auto-delivery for high cell density cultivations in microplates and shake flasks, Microbial Cell Factories 2008, 7:31; published Nov. 18, 2008.*
Soini et al., High cell density media for *Escherichia coli* are generally designed for aerobic cultivations—consequences for large-scale bioprocesses and shake flask cultures, Microbial Cell Factories 2008, 7:26.*
International Preliminary Report on Patentability for corresponding PCT/EP2010/052780 mailed Sep. 15, 2011, six pages.
Asenjo et al: "Optimization of Batch Processes Involving Simultaneous Enzymatic and Microbial Reactions," Biotechnology and Bioengineering, vol. 37 (1991), pp. 1087-1094.
Asenjo et al "Optimal Control of Batch Processes Involving Simultaneous Enzymatic and Microbial Reactions," Bioprocess Engineering, vol. 14 (1996), pp. 323-329.
Written Opinion of the International Searching Authority for corresponding PCT/EP2010/052780 mailed Jun. 21, 2010, four pages.
Panula-Perla La Johanna et al; "Enzyme controlled glucose auto-delivery for high cell density cultivations in microplates and shake flasks"; Microbial Cell Factories, Biomed Central, London, NL, vol. 7, No. 1; Nov. 18, 2008; p. 31; XP021043554.

* cited by examiner

*Primary Examiner* — Karen Cochrane Carlson
*Assistant Examiner* — Jennifer M. H. Tichy
(74) *Attorney, Agent, or Firm* — Rankin, Hill & Clark LLP

(57) ABSTRACT

The present invention is generally in the field of continuous and high-cell-density cultivation in laboratory- or large-scale liquid shaken cultures. More particularly it relates to a method of enzyme-based fed-batch (EnBase) for liquid microbial prokaryotic or eukaryotic cell cultivation having the possibility to manipulate the growth rate of the cultured organisms by a controlled enzymatic release of the growth-limiting substrate-monomer from substrate-polymers or substrate-oligomers.

20 Claims, 6 Drawing Sheets

ENZYME-BASED FED-BATCH TECHNIQUE IN LIQUID CULTURES

FIELD OF THE INVENTION

The present invention is generally in the field of continuous and high-cell-density cultivation in laboratory- or large-scale liquid shaken cultures. More particularly it relates to a method of enzyme-based fed-batch (EnBase) for liquid microbial prokaryotic or eukaryotic cell cultivation having the possibility to manipulate the growth rate of the cultured organisms by a controlled enzymatic release of the growth-limiting substrate-monomer from substrate-polymers or substrate-oligomers.

BACKGROUND OF THE INVENTION

Most cultivation methods for the growth of microbial prokaryotic or eukaryotic cells are based on the cultivation in a liquid medium. In practice, such liquid cultures are performed in a batch process operational mode. The batch process is a discontinuous process, where the sterile growth medium with all required substrates is initially inoculated with a pure culture of microbial prokaryotic or eukaryotic cells and no additional growth medium is added during the course of operation. This means, that the batch process is a partially closed system, wherein the only material added and removed during the course of operation is air/gas exchange, antifoam and pH controlling agents (Cinar A. et al., Batch fermentation—modeling, monitoring, and control, 2003, Marcel Dekker Inc., page 5). These batch cultures are continuously shaken or stirred to keep a desired degree of homogeneity of the substrates and cells to guarantee as high as possible oxygen transfer for aerobic cultures. These non-controlled shaken batch cultures, however, have substantial disadvantages, e.g. the high initial substrate concentrations in the growth medium. This high initial substrate concentration leads to long adaptation phases (lag phases) of the microbial prokaryotic or eukaryotic cells, which are especially relevant in enrichment cultures, e.g. in food diagnostics. In high substrate concentrations the microbial prokaryotic or eukaryotic cells may respond with overflow metabolism and secretion of large amounts of by-products, mainly acetate, ethanol, and lactate. Non-controlled growth also easily leads to oxygen deprivation and if anaerobic conditions occur the microbial prokaryotic or eukaryotic cells also secrete formate, succinate, hydrogen, and additional $CO_2$ (Luli W. R. & W. R. Strohl, Appl. Environ. Microbiol., 1990, 56:1004-1011; Riesenberg D. et al., J. Biotechnol., 1991, 20:17-28). Thus, anaerobic metabolism (fermentation reactions) and overflow metabolism cause a drift of pH and secretion of fermentation products in amounts, which may inhibit the growth of microbial prokaryotic or eukaryotic cells and impair recombinant protein production. Some of these metabolites are also synthesized under aerobic conditions if increasing concentrations of substrates, e.g. carbohydrates, repress the genes of respiration. Thus, cells which normally grow fast with oxygen as terminal electron acceptor, will show growth inhibition and side metabolite accumulation (ethanol), even under aerobic conditions (glycolysis) when the substrate concentration is high, a phenomenon called "Crabtree effect" (Crabtree H. G., J. Biochem., 1928, 22:1289-1298; Rinas U. et al., Appl. Microbiol. Biotechnol., 1989, 31:163-167). Long-term exposure to high substrate concentrations is characterized by catabolite repression; the substrates that provide the cells with the most energy and growth advantage are selectively taken up, whereas various functions involved in the catabolism and uptake of the less preferred substrates are repressed (Monod J., Actualites scientifiques et industrielles, 1942, 911:70-78). This leads to low biomass yield, and poor quality and quantity of microbial prokaryotic or eukaryotic cell products. The biomass yield in shaken *Escherichia coli* cultures is typically only in the range of 1-2 g dry cells per liter in shake flask cultures, and in microscale often much lower. Thus, high cell densities are not achieved with the batch technology.

In order to avoid the above mentioned effects of high initial substrate concentration, most large-scale cultivations in bioreactors apply the fed-batch technology (Kleman G. L. & Strohl W. R., Curr. Opin. Biotechnol., 1994, 5:180-186; Riesenberg D., Curr. Opin. Biotechnol., 1991, 2:380-384). Fed-batch cultivation is distinguished from batch cultivation by the addition of a defined amount of fresh growth-limiting substrate in highly concentrated form, mostly by continuous feeding (Kleman G. L. & Strohl W. R., Curr. Opin. Biotechnol., 1994, 5:180-186). In industrial practice the process efficiency can be increased by regular withdrawal of the cultivation broth, a procedure which is called repeated fed-batch (Longbardi G. P., Bioproc. Engin., 1994, 10:185-194). Oxygen limitation, pH drift and the inhibition of growth due to fermentation by-products can be avoided with continuous substrate feeding because the oxygen consumption increases relative to the substrate consumption rate and the growth rate of the culture. With well-controlled substrate feeding, high cell densities with up to 50-fold higher biomass compared to batch cultivations can be produced in commonly used industrial bioreactors. *E. coli* cultures can reach final biomass concentrations of more than 100 g dry cells per liter (Lee S. Y., Trends Biotechnol., 1996, 14:98-105; Riesenberg D., Curr. Opin. Biotechnol., 1991, 2:380-384). Although the fed-batch technology is very well applicable in industrial bioreactors, it is not easily applicable for small laboratory-scale shaken cultures. Thus, alternative fed-batch cultivation strategies have been developed. In the following a difference is made between 1) growth-limiting substrate-monomers, which are metabolically active, 2) substrate-oligomers, and 3) substrate-polymers, which are metabolically inactive.

For example, in the field of medical technology drugs are often supplied by the fed-batch slow-release technique, also called delivery systems. These systems are based on the slow release of a metabolically active growth-limiting substrate-monomer by diffusion from a solid phase, e.g. from artificial polymer matrices, over a long period of time. Such polymer matrices can also be packed with nutrient components and they can be added to cultivation vessels. With such a fed-batch slow-release technique, Lübbe C. et al. (Appl. Microbiol. Biotechnol., 1985, 22:424-427) fed ammonia to *Streptomyces clavuligerus* cultivation from ethylene-vinylacetate copolymer discs containing $NH_4Cl$ to study $NH_4^+$ control and to increase the production of cephalosporins in comparison to batch cultures. However, the authors did not observe significant advantage of applying their fed-batch slow-release system because they were not able to match the exponential growth of the cells with a fixed, linear feed of the growth-limiting substrate-monomer. Furthermore, Jeude M. et al. (Biotechnol. Bioeng., 2006, 95:433-445) used silicone elastomer (polydimethylsiloxane) discs as a solid phase containing the growth-limiting substrate-monomer to create fed-batch like conditions for cultivations (see also Büchs J. et al., WO2006/119867). Although the authors observed minimization of overflow metabolism, which resulted in a higher biomass yield, these systems are rarely applied in microbial prokaryotic or eukaryotic cell cultivations. This is because only relatively small amounts of the growth-limiting substrate-monomer can be packed into such solid phases. Furthermore, the substrate-monomer release rate from such a solid phase is usually fastest at the beginning of the cultivation, when the amount of microbial prokaryotic or eukaryotic cells is lowest and the risk for overflow metabolism is highest. Thus, the fed-batch slow-release cultivation approaches based on solid phases that directly release the growth-limiting substrate-monomer into the medium are limited with regards to the scalability, i.e. to the amount of the growth-limiting substrate-monomer that can be packed to the system and the possibilities to accurately control the substrate-monomer release. Moreover, such solid phases are not easy to produce, which limit their applicability.

The enzyme-based fed-batch system of Vasala A. et al. (PCT/FI2007/050648) offers a much better capacity and an excellent control of substrate release and microbial prokaryotic or eukaryotic cell growth (see also Panula-Perälä J. et al., 2007, J. Biotechnol., 131S:S182—Issue for the 13th European Congress of Biotechnology, Barcelona, Spain, poster no. 91.-doi:10.1016/j.jbiotec.2007.07.920, Panula-Perälä et al., 2008, Microb. Cell Fact. 7:31). There, a fed-batch technology is described, having a liquid phase and a solid phase, i.e. a two-phase system. In difference to the previous approaches the solid phase, e.g. a gel phase, provides a source of a metabolically inactive substrate-polymer, which delivers the metabolically active substrate-monomer by biocatalytic degradation, i.e. enzyme-based. In this system the delivery rate of the growth substrate and thus the growth rate of the microbial prokaryotic or eukaryotic cells can be simply controlled by the concentration of the substrate-polymer degrading enzyme. Such a system has advantages in comparison to usual fed-batch slow-release systems comprising a solid phase because the release of the growth-limiting substrate-monomer to the liquid phase is retarded and can be simply controlled. With this method a high amount of substrate-polymer can be packed into the system. Furthermore, the gel-formulation as the solid phase ensured that most of the substrate-polymer is maintained in a water-soluble form. Thus, high cell densities are supported without impairing the physical properties of the liquid phase. However, this system has also disadvantages insofar as starch immobilized into a gel is slowly diffusing into a liquid phase, and simultaneously being degraded enzymatically. In addition, the capacity of the gel seriously limits the amount of starch that can be applied to the system. Due to the presence of a gel, not only the enzyme amount but also the starch diffusion rate determines the reaction speed. Too fast starch diffusion may result in accumulation of insoluble starch into the liquid phase which has negative effects on the cell growth.

All the fed-batch systems described above are composed of a two-phase system providing a liquid phase, which contains the microbial prokaryotic or eukaryotic cells and the cultivation medium, and a solid phase, which contains the growth-limiting substrate-monomer or the substrate-polymer. However, two-phase systems are not easy to use in biotechnological applications where frequent (automatic) samplings or measurements are needed. This means that two-phase systems are not only complicated to produce but also limited in their applicability in many biotechnological applications, e.g. laboratory-scale. This may explain why such systems have not become popular in simple cultivations of the biotechnologically most important bacterial species, E. coli.

For microbial prokaryotic or eukaryotic cells, which cannot efficiently degrade substrate-polymers in the medium, a method of partial or complete enzymatic degradation of substrate-polymers has been developed to enhance their growth rate. For example, Tokuda M. et al. (J. Ferment. Bioeng., 1998, 85:495-501) showed that anaerobic methane fermentation of whiskey distillery waste can be enhanced by partial digestion of starch (substrate-polymer) with enzymes or with moulds prior to anaerobic methane production process. This kind of enzymatic pretreatment, however, is not suitable to provide a controlled cultivation for obtaining high cell densities of microbial prokaryotic or eukaryotic cells.

Another interesting application for the cultivation of eukaryotic cells has been presented by Green H. & J. G. Rheinwald (U.S. Pat. No. 3,926,723). The aim of the authors was to improve the cell yield in mammalian cell cultures by decreasing the accumulation of harmful metabolites. The authors reasoned that low concentrations of the growth-limiting substrate-monomer (glucose) cannot be maintained by direct addition to the medium because the growing cells consume them rapidly. Therefore, they used small amounts of a substrate-polymer (starch) in a liquid medium and activities of hydrolytic enzymes (e.g. amylase and maltase) present in horse, pig, or bovine serum to release growth-limiting monomers (glucose), i.e. cultivations were done in rich medium containing serum. This is no chemically defined medium and makes it impossible to control the cell growth. The authors used only 1 g/l of starch, which in theory would support at most 1 g dry cells per liter of biomass (cells). In practice, cell yields remained considerably lower because starch easily looses its solubility and digestibility in water-based liquids. As a result, no significant increase of cell number was obtained. Thus, one can conclude that such technique was not used for controlling or enhancing the growth rate of eukaryotic cells but to prevent the accumulation of harmful metabolites (e.g. lactic acid) as a growth-retarding compound. Therefore, it cannot be regarded as a method for enzyme-based fed-batch high-cell-density cultivation.

Another approach where enzymatic degradation of cellulosic material was used to provide a carbon source for microorganisms has been described by Asenjo et al. (Asenjo et al., Biotechnology and Bioengineering, Vol. 37 (1991), pp. 1087-1094; Asenjo et al., Bioprocess Engineering 14 (1996), pp. 323-329) Their research was run to optimize product formation by minimizing the accumulation and inhibitory effect of intermediate compounds (glucose or cellubiose). Asenjo et al. optimized enzyme feeding so that enzyme-inhibiting compounds will not accumulate. This approach, however, does not lead to high cell density cultivation The object of the present invention is to provide a method for continuous and high-cell-density microbial prokaryotic or eukaryotic cell cultivation in laboratory- or large-scale liquid shaken cultures having the possibility to control the growth rate of the cultured organisms by a controlled enzymatic release of the growth-limiting substrate-monomer from substrate-polymers or substrate-oligomers.

SUMMARY OF THE INVENTION

The technical problem forming the basis of the invention is the provision of a method for controlling the growth-rate of microbial prokaryotic or eukaryotic cells in laboratory- or large-scale liquid shaken cultures medium to high cell densities by the enzyme-based fed-batch technique (EnBase). This means that a liquid system is provided in which metabolically inactive substrate-polymers or substrate-oligomers are converted to a fully soluble metabolically active growth-limiting substrate-monomer during cultivation by the treatment with digestive enzymes in order to slowly release the growth-limiting substrate-monomer into the medium. Thus, the growth-limiting substrate-monomer is released in a controlled way from a substrate-polymer or a substrate-oligomer into the medium by enzymatic action.

DEFINITIONS

Figure 1:
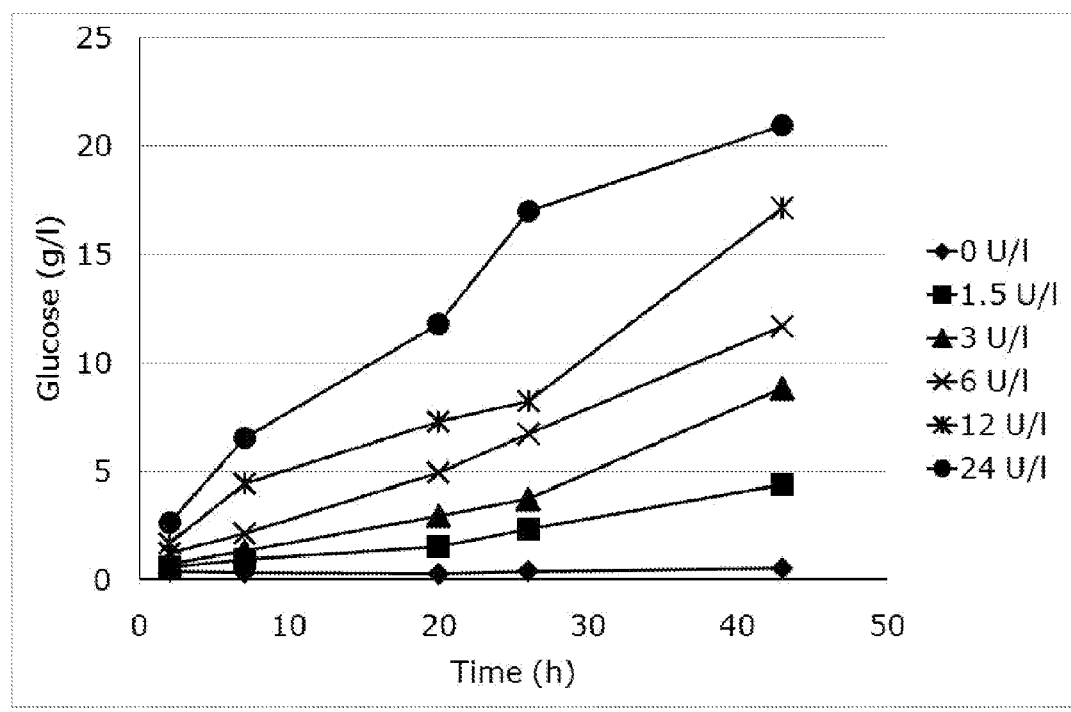
FIG. 1 illustrates graphically the release rate of the growth-limiting substrate-monomer glucose from the substrate-polymer dextrin in liquid mineral salt medium. The glucose release rate depends on time and the concentration of the enzyme glucoamylase (E.C. 3.2.1.3.).

As used herein, "microbial", refers to organisms, also known as "microorganisms", that are microscopic, i.e. usually too small to be seen by the naked human eye.

As used herein, "prokaryotic cells" or "microbial prokaryotic cells", also known as "prokaryotes", refer to a group of mostly unicellular organisms that lack a nucleus, also known as karyon, or any other membrane-bound organelles. The prokaryotes are divided into two domains, i.e. archaea (archaebacteria) and bacteria (eubacteria).

As used herein, "eukaryotic cells", also known as "eukaryotes", refer to organisms, whose cells are organized into complex structures enclosed within membranes, e.g. the nucleus. "Microbial eukaryotic cells" are not only protists (yeasts and unicellular algae) and fungi, which are most commonly unicellular and microscopic, but also microscopic animals and plants, which are multicellular.

As used herein, "cell culture" or "cell cultivation" is a method of multiplying microbial organisms, i.e. by which microbial prokaryotic or eukaryotic cells are grown under controlled laboratory conditions, whereas "eukaryotic cell culture" additionally refers to planktonic cultivation of higher eukaryotic cells and also includes tissue cultures, which involves the growth of tissues explanted from a multicellular eukaryotic organism.

"Eukaryotic cell cultures" also include cell suspension cultures like CHO (Chinese Hamster Ovary) cell cultures where no tissues are formed.

As used herein, "pure culture" refers to a culture of microbial prokaryotic or eukaryotic cells containing a single clone or species of an organism.

As used herein, "high cell density" refers to a cultivation which yields a high number of microbial prokaryotic or eukaryotic cells in a defined period of cultivation. The high-cell-density value is dependent on the microbial cell and can be defined as the cell density value that is reached with gradual addition of growth-limiting substrates (fed-batch) without intoxicating the microbe, i.e. a viable cell concentration of $3 \times 10^9$ cells/ml, preferably above $1 \times 10^{10}$ cells/ml of E. coli.

As used herein, "laboratory-scale" liquid cultures refer to cultivation of microbial prokaryotic or eukaryotic cells in bioreactors or the like in the range of 500 ml to 10 l, shake flasks or the like in the range of 10 to 1000 ml, in cuvettes, glass vials, falcon tubes or the like in the range of 1 to 100 ml, in microtiter plates, microbioreactors or the like in the range of 5 µl to 1 ml.

As used herein, "large-scale" liquid cultures refer to cultivation of microbial prokaryotic or eukaryotic cells in cultivation vessels from 10 liters up to 200 $m^3$, preferably 100 liter to 100 $m^3$, more preferably 100 to 1000 liters. They are typically performed in bioreactors (e.g. stirred tanks), but can also include simple (disposable) containers like plastic bags of up to few cubic meters.

As used herein, "batch" cultivation is a discontinuous process, where the sterile growth medium with all substrates required is initially inoculated with a pure culture of microbial prokaryotic or eukaryotic cells and no additional growth medium is added during the course of operation. This means, that the batch process is a partially closed system, wherein the only material added and removed during the course of operation is air/gas exchange, antifoam and pH controlling agents. The batch cultures are continuously shaken or stirred to keep a desired degree of homogeneity of the substrates and cells and to guarantee an as high as possible oxygen transfer for aerobic cultures.

As used herein, "fed-batch" cultivation is a process, where a certain amount of fresh growth-limiting substrates is continuously added to the cultivation medium to provide their low concentrations in cultivation media and to obtain control of the growth of microbial prokaryotic or eukaryotic cells. The "enzyme-based fed-batch technique" or "EnBase" refers to a technique by which the growth-limiting substrate-monomer is slowly released from a substrate-polymer or substrate-oligomer either by diffusion or enzymatic degradation from a solid phase or by enzymatic degradation from a water soluble or partly soluble substrate-polymer or substrate-oligomer containing in the liquid phase. In this case the substrate-polymer or substrate-oligomer can be added continuously or discontinuously to the culture, but referentially is added at the beginning of the culture. In this regard it is also possible to add one or more portions of the substrate-polymer or substrate-oligomer during the fermentation and "boost" with enzyme depending on the growth.

As used herein, the "solid phase" refers either to an artificial polymer matrix or rather reservoir, also known as "discs", e.g. ethylene-vinylacetate copolymer or silicone elastomer, or to a "gel phase". As used herein, the "gel phase" refers to a semisolid artificial polymer matrix or rather reservoir, e.g. immobilized starch strengthened with agar.

As used herein, the "liquid phase" refers to any suitable liquid phase capable of acting as the cultivation medium.

Examples of the liquid phase include various commonly used chemically defined media, e.g. mineral salt medium. The liquid phase comprises not only the components of the mineral salt medium but also the microbial prokaryotic or eukaryotic cells. In the present invention, the liquid phase also comprises the substrate-polymer or the substrate-oligomer and the enzymes for its degradation.

As used herein, the "substrate" refers to any suitable substance, which affects the cultivated organisms' capability to grow.

As used herein, the "substrate-monomer" refers to a metabolically active growth component, which can be efficiently degraded by the microbial prokaryotic or eukaryotic cells of the culture. In the present invention, the substrate-monomer is "growth-limiting", which means that the substrate-monomer is present in a low proportion in relation to the other ingredients and that it is exhausted first.

Preferably the "substrate-polymer" or "substrate-oligomer" is water-soluble.

As used herein, the "substrate-polymer" or "substrate-oligomer" refers to a metabolically inactive growth component, which cannot be efficiently degraded by the microbial prokaryotic or eukaryotic cells of the culture. Preferably the "substrate-polymer" or "substrate-oligomer" has minimum length of two monomers.

As used herein, the "enzymes" refer to all enzymes known in the art capable of degrading the substrate-polymer or substrate-oligomer of the present invention for the release of the growth-limiting substrate-monomer to provide fed-batch conditions. For enzymatic degradation of the substrate-polymer or substrate-oligomer, either individual enzymes or combinations of different enzymes, i.e. enzyme cocktails can be applied.

As used herein, the "glucose polymer" refers to homopolymers or heteropolymers. The "homopolymer" refers to a glucose polymer, which consists of D-glucose monomers linked by glycosidic bonds and the "heteropolymer" refers to a compound comprised of different monosaccharides or aminosugars, e.g. hemicellulose.

As used herein, the "starch" refers to a glucose polymer, which consists of two classes of high-molecular weight glucose polymers: amylose (mainly non-branched α-1,4-bonded polymer) and amylopectin (branched molecule with a higher content of α-1,6-glycosidic bonds).

As used herein, the "dextrin" refers to a starch derivative being a mixture of linear α-(1,4)-linked D-glucose polymers starting with an α-(1,6)-glucose.

As used herein, the "cellulose" refers to linear β-(1,4)-linked D-glucose polymer. Suitable cellulose derivatives include methylcellulose or carboxymethylcellulose.

As used herein, the "soluble oligosaccharides and disaccharides" refer to compounds such as cellobiose, which consists of two glucose molecules linked in a β-(1,4)-bond, or sucro-se, also known as saccharose and α-D-glucopyranosyl-(1↔2)-β-D-fructofuranosid, a disaccharide of glucose and fructose.

DETAILED DESCRIPTION OF THE INVENTION

The present invention provides the enzyme-based fed-batch technique (EnBase) aiming to high-cell-density cultivation of microbial prokaryotic or eukaryotic cells in laboratory- or large-scale liquid shaken cultures. Therefore, an easy solution for a scalable high-cell-density process of microbial prokaryotic or eukaryotic cells in liquid medium is provided, even for the recombinant protein production. This enzyme-based fed-batch technique, also known as "enzyme-based substrate delivery technique", in a liquid culture is a feasible alternative to two-phase enzyme-based fed-batch techniques based on substrate-binding polymers or gels.

In one embodiment, the enzyme-based fed-batch technique is performed in laboratory-scale liquid shaken cultures having a volume in the range from 5 µl to 100 l. More preferably, cultivation in bioreactors or the like in the range of 500 ml to 100 l, shake flasks or the like in the range of 10 to 500 ml, in cuvettes, glass vials, falcon tubes or the like in the range of 1 to 10 ml, in microtiter and deepwell plates, microbioreactors or the like in the range of 5 µl to 5 ml.

In another embodiment, the enzyme-based fed-batch technique is performed in a large-scale liquid culture in an industrial stirred tank bioreactor having a volume range from 10 liters to 200 m$^3$.

In still another embodiment, the cultivation is performed in a 500 liters plastic bag (WAVE Bioreactor, Wave Europe). By the enzyme-based fed-batch technique from a soluble substrate-polymer or substrate-oligomer, formation of heterogenic environment, i.e. local compartments with high or low substrate concentration inside the bioreactor, can be avoided and improved cell yield can be obtained.

In the present invention, the enzyme-based fed-batch technique is preferably performed in a liquid mineral salt medium containing a substrate-polymer or substrate-oligomer that is subjected to enzymatic degradation for slowly releasing the growth-limiting substrate-monomer in high-cell-density laboratory- or large-scale liquid shaken cultures of microbial prokaryotic or eukaryotic cells.

An exemplary mineral salt medium comprises 2 g/l $Na_2SO_4$, 2.68 g/l $(NH_4)_2SO_4$, 0.5 g/l $NH_4Cl$, 14.6 g/l $K_2HPO_4$, 3.6 g/l $NaH_2PO_4 \cdot H_2O$, 1.0 g/l $(NH_4)_2$—H-citrate, 1.5 M $MgSO_4$ (MSM; Neubauer P. et al., Biotechnol. Bioeng., 1995, 47:139-146). Optionally, low amounts of tryptone (0.24 g/l) and yeast extract (0.48 g/l) can be added to shorten the adaptation period (lag-phase) of microbial prokaryotic or eukaryotic cells to mineral salt medium. These components in low amounts will not disturb the enzyme-based fed-batch technique, although they can be utilized as carbon and energy source by microorganisms. The substrate-polymer or substrate-oligomer is added in concentrations from 10 to 50 g/l, preferably 10, 20, 30, 40, 50 g/l, most preferably 40 g/l. The components were mixed with 1 liter of distilled water, autoclaved and cooled. Afterwards, the basal medium was supplemented with 3 mM $MgSO_4$, 2 ml/l of trace element solution (Holme T. et al., Process Biochem., 1970, 5:62-66) and 0.1 g/l of thiamine hydrochloride. In another embodiment, the liquid mineral salt medium is completed with MOPS-buffer ((3-(N-morpholino)propane-sulfonic acid, pH-range 6.5-7.9; 20 mM, medium pH 7.0). In another further embodiment, the liquid mineral salt medium can be further supplemented or boosted in later phases of the process by various amounts of tryptone and yeast extract to improve the synthesis of recombinant proteins.

The above mentioned liquid mineral salt medium is to be understood as a preferred example. As the mineral salt medium any defined medium known in the art for microbial prokaryotic or eukaryotic cell growth may be suitable.

In one embodiment, the present invention provides methods for quick medium preparations. More preferably, for the preparation of pre-sterilized ready-made liquid mineral salt medium, pre-sterilized ready-made mineral salt medium powder, pre-sterilized ready-made mineral salt medium tablets, or pre-filled or coated cultivation vessels with pre-sterilized liquid or dry mineral salt medium.

In one embodiment, the substrate is a water-soluble substrate-oligomer or substrate-polymer. In another embodiment, the substrate-polymer or substrate-oligomer is a gel-forming or only partly soluble polymer or oligomer. Preferably, the substrate-polymer is a water-soluble glucose polymer, also known as glucan. Glucans can be made water soluble via limited hydrolysis by enzymatic treatment, i.e. acid or alkali, by heat treatment (which is usually, however, a reversible process) or by chemical modifications of some functional groups. More preferably, the substrate-polymer is a water-soluble glucose homopolymer, e.g. cellulose (β-1,4-glucan), curdlan (β-1,3-glucan), dextran (α-1,6-glucan), glycogen (α-1,4- and α-1,6-glucan), laminarin (β-1,3- and β-1,6-glucan), lentinan (β-1,6:β-1,3-glucan), lichenin, pleuran (β-1,3- and (β-1,6-glucan), pullulan (α-1,4- and α-1,6-glucan), starch (α-1,4- and α-1,6-glucan), and zymosan (β-1,3-glucan).

The substrate-polymer or substrate-oligomer is enzymatically degraded to the growth-limiting substrate-monomer or another readily assimilable compound by the controlled addition of at least one degrading enzyme or by a mixture of two or more degrading enzymes. More preferably, by an enzymatic activity which is not present in the cultured microbial prokaryotic or eukaryotic cells. In one embodiment, the substrate-polymer or substrate-oligomer is partly degraded during cultivation. In another embodiment, the substrate-polymer or substrate-oligomer is completely degraded during the cultivation. The controlled release of the substrate-monomer from the substrate-polymer or substrate-oligomer is preferably adjusted by the enzyme concentration or the enzyme activity of either one enzyme or a mixture of enzymes. The amount of enzyme to be used depends from the oxygen content of the culture and preferably should be measured during the cultivation process. If cells grow slowly and oxygen level stays high, more enzyme can be added. If the oxygen content in the culture medium becomes too low, i.e. anaerobic conditions (which are detrimental to the cell growth) may occur, no further enzyme should be added but instead aeration should be improved. The oxygen content measurement and the decision how much enzyme has to be added is well known to a person skilled in the art.

The preferred enzyme(s) depends on the raw material. For applications, where a constant growth-limiting substrate-monomer release from a substrate-polymer or substrate-oligomer is required, exo-enzymes digesting the end (reduced or non-reduced) of the substrate-polymer or substrate-oligomer are preferred. For glucose-polymers rich in alpha-1,4-linkages, glucoamylases are such enzymes. For glucans rich in alpha-1,6-linkages, debranching enzymes like isoamylases may be needed. For glucans rich in beta-1,4-linkages, beta-glucosidases and other cellulolytic enzymes are needed. The selection of the most suitable enzyme for degrading the substrate-polymer or substrate-oligomer is well known to a person skilled in the art.

In one embodiment, soluble starch derivatives are potent substrate-polymers for the high-cell-density cultivation of microbial prokaryotic or eukaryotic cells, which cannot directly use soluble starch derivatives as a substrate. Glucose can be produced from starch by the addition of the enzymes alpha- and gamma-amylase.

In one embodiment, dextrin is a potent substrate-polymer for the high-cell-density cultivation of microbial prokaryotic or eukaryotic cells, which cannot use dextrin as a substrate. Dextrin is produced by the limited enzymatic hydrolysis of starch or rather amylopectin with the enzyme alpha-amylase. The glucose monomers can be produced from dextrin by the addition of the enzyme glucoamylase that is also known as gamma-amylase or amyloglucosidase. Glucose production may be further enhanced by action of other amylases (e.g., alpha-amylases, isoamylases). In another embodiment, maltose, maltotriose and other short α-1,4-linked glucose polymers, which can be also digested with glucoamylase can be used instead of starch or dextrin as potent substrate-polymers for the high-cell-density cultivation of microbial prokaryotic or eukaryotic cells.

In one embodiment, water-soluble cellulose derivatives are potent substrate-polymers for the high-cell-density cultivation of microbial prokaryotic or eukaryotic cells, which cannot directly use water-soluble cellulose derivatives as a substrate. Water-soluble cellulose derivatives are produced by enzymatic degradation of the crystalline structure of cellulose by endocellulases, thus, exposing the ends of glucan chains to exo-cellulases, which cut 2-4 glucose groups from the ends (including the disaccharide cellobiose). Controlled glucose production can be achieved by the addition of beta-1,4-glucosidase, also known as cellobiase, that hydrolyzes cellobiose. In another embodiment, "methylcellulose or carboxymethylcellulose", which are created by adding methyl or carboxymethyl groups to replace some of the hydroxyl groups of the glucopyranose monomers of the cellulose backbone, can be used as potent substrate-polymers for the high-cell-density cultivation of microbial prokaryotic or eukaryotic cells, which cannot directly use methylcellulose or carboxymethylcellulose as a substrate. The methylcellulose or carboxymethylcellulose, however, is often capable of forming gels in water solutions. To further improve the applicability of the methylcellulose or carboxymethyl-cellulose-containing medium, the viscosity (gel-like structure) can be reduced by preliminary treatment of the material with a cellulase mixture containing exocellulases and endocellulases, but a very low amount of beta-1,4-glucosidase activity. Such cellulase formulations can be obtained from mould *Trichoderma* fermentation (e.g. by Novozymes, Bagsværd, Denmark).

In one embodiment, heteropolymers are potent substrate-polymers for the high-cell-density cultivation of such microbial prokaryotic or eukaryotic cells, which cannot directly use heteropolymers as a substrate. Hemicellulose can be any of several heteropolymers, also known as matrix polysaccharides, present in almost all plant cell walls along with cellulose. Such compounds can be either partly or completely utilized by microbial prokaryotic or eukaryotic cells. Hemicellulose has a random, amorphous structure with little strength and is, therefore, easily hydrolyzed by dilute acid or base as well as myriad of hemicellulase enzymes.

In one embodiment, soluble oligosaccharides and disaccharides are potent substrate-polymers or substrate-oligomers for the high-cell-density cultivation of microbial prokaryotic or eukaryotic cells, which cannot directly use soluble oligosaccharides and disaccharides as a substrate, e.g. cellobiose or sucrose. The disaccharide cellobiose can be split to two monomer-molecules glucose when cellobiase enzymes are added. The disaccharide sucrose can be split to two monomer-molecules glucose and fructose by the addition of the enzyme invertase, also known as saccharase or beta-fructofuranosidase.

The following improvements could be obtained with the enzyme-based fed-batch technique developed in the present invention:
1) Preparation of the nutrient-delivery system becomes easier.
2) Since the substrate for nutrient-producing enzyme(s) remains completely soluble in the liquid phase, the oxygen transfer capacity of the medium or the metabolic capacity of the organisms is not changed during the cultivation process.

3) Sampling and analysis become easier, since membrane discs or gel are not required.
4) Separation of microbial prokaryotic or eukaryotic cell products becomes easier, since the medium does not contain any material co-sedimenting with the cells.

With proper enzymatic treatment (either pre-treatment or in-situ treatment), a high utilization level of the substrate can be obtained.

EXAMPLES

The compositions and methods and preparations and use thereof described herein are further described by the following examples.

Example 1

Glucose Release Rate from Dextrin

The glucose release-rate from dextrin was conducted in a liquid mineral salt medium containing dextrin as the substrate-polymer and the dextrin-degrading enzyme glucoamylase at different concentrations.

The liquid system for the measurement of the glucose release was based on a liquid mineral salt medium (MSM; Neubauer P. et al., Biotechnol. Bioeng., 1995, 47:139-146), which comprises: 2 g $Na_2SO_4$, 2.7 g $(NH_4)_2SO_4$, 0.5 g $NH_4Cl$, 14.6 g $K_2HPO_4$, 3.6 g $NaH_2PO_4 \cdot H_2O$, 1.0 g $(NH_4)_2$—H-citrate. For the present experiment, 40 g/l soluble dextrin was added as the substrate-polymer. The components were mixed with 1 liter of distilled water, autoclaved and cooled. Afterwards, the basal medium containing dextrin was supplemented with 3 mM $MgSO_4$, 2 ml/l of trace element solution (Holme T. et al., Process Biochem., 1970, 5:62-66) and 0.1 g/l of thiamine hydrochloride. The liquid medium, i.e. 150 μl-aliquots, was distributed into sterile 96-well polysterene microtiter plate (Perkin Elmer Spectra™-96 TC, Waltham, USA). The respective amounts of glucoamylase from *Aspergillus niger* (E.C. 3.2.1.3.; Amylase AG 300L, Novozymes, Bagsværd, Denmark), i.e. 0, 1.5, 3, 6, 12, 24 or 48 U/l, were added and the experiment was immediately started at 37° C. on an orbital shaker (180 rpm). The concentration of the glucose released during glucoamylase digestion was analyzed with YSI 2700 Select Biochemical Analyzer (YSI Inc., Yellow Springs, USA).

The results show a clear dependency of glucose accumulation on the glucoamylase amount in the liquid mineral salt medium over the tested range of enzyme concentrations (FIG. 1). Without the addition of glucoamylase, no glucose release was observed, whereas 24 U/l glucoamylase gave the highest glucose release rate of approximately 17 g/l and 21 g/l during 24 and 43 hours of incubation, respectively. Thus, for enzyme-based fed-batch type cultivation experiments with *E. coli* a glucoamylase amount of 3 to 24 U/l can be proposed as a good starting point, assuming that a release of 5 to 10 g/l glucose over a time period of 30 hours would be related to an overall specific growth rate of $0.2 \pm 0.1$ h$^{-1}$. Based on these calculations, and considering a yield coefficient of 0.5 g cells dry weight per one gram of glucose, a culture inoculated with an $OD_{600}$ of 0.1 should grow up to an $OD_{600}$ of 8 to 16 within 30 hours.

Example 2

Enzyme-Based Fed-Batch Cultivation of *E. coli* in Liquid Mineral Salt Medium Containing Dextrin and the Enzyme Glucoamylase Effects of different amounts of the enzyme glucoamylase on the growth of *E. coli* BL21(DE3) in liquid mineral salt medium containing dextrin. Cultivations were performed in 48 deep-well plates (Ritter, Germany) with 1.5 ml culture volumes per each well.

A liquid mineral salt medium (MSM; Neubauer P. et al., Biotechnol. Bioeng., 1995, 47:139-146) was used as the general base for the cultivation medium, which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4 \cdot H_2O$, 1.0 g $(NH_4)_2$—H-citrate, 0.24 g tryptone, 0.48 g yeast extract. For present experiment, 40 g/l soluble dextrin was added as carbon and energy source, i.e. as the substrate-polymer. The components were mixed with 1 liter of distilled water, autoclaved and cooled. Prior to inoculation, the basal medium containing dextrin was supplemented with 3 mM $MgSO_4$, 2 ml/l of trace element solution (Holme T. et al., Process Biochem., 1970, 5:62-66) and 0.1 g/l of thiamine hydrochloride. Cultivation experiments were performed using a pure culture of *E. coli* strain BL21(DE3). The precultures were prepared by washing bacteria from freshly-cultivated Luria Bertani (LB)-plates with mineral salt medium (2 ml per plate) containing neither glucose nor dextrin. The plate washout was used as an inoculants to yield initial cell density of $OD_{600}=0.1$ in each cultivation well.

For cultivation, 1.5 ml-aliquots of the MSM medium containing dextrin were distributed into sterile 48-well polysterene deepwell-plates (Ritter, Germany) having a total volume of 5 ml. The respective amounts of glucoamylase from *Aspergillus niger* (E.C. 3.2.1.3.; Amylase AG 300L, Novozymes, Bagsværd, Denmark), i.e. 0, 1.5, 3, 6, 12, 24 or 48 U/l, were added after inoculation and the culture was immediately started at 37° C. on an orbital shaker (180 rpm). Cell growth was followed with a spectrophotometer after the dilution of culture samples in growth medium with a Victor$^3$ Multiwell Plate Reader (Perkin Elmer, Waltham, USA) at a wavelength of 490 nm. The results were converted to $OD_{600}$ values according to a standard curve. One unit of $OD_{600}$ corresponds to a dry cell weight of 0.3 g/l (Soini J. et al., Microb. Cell Fact., 2008, 7:26).

Figure 2:
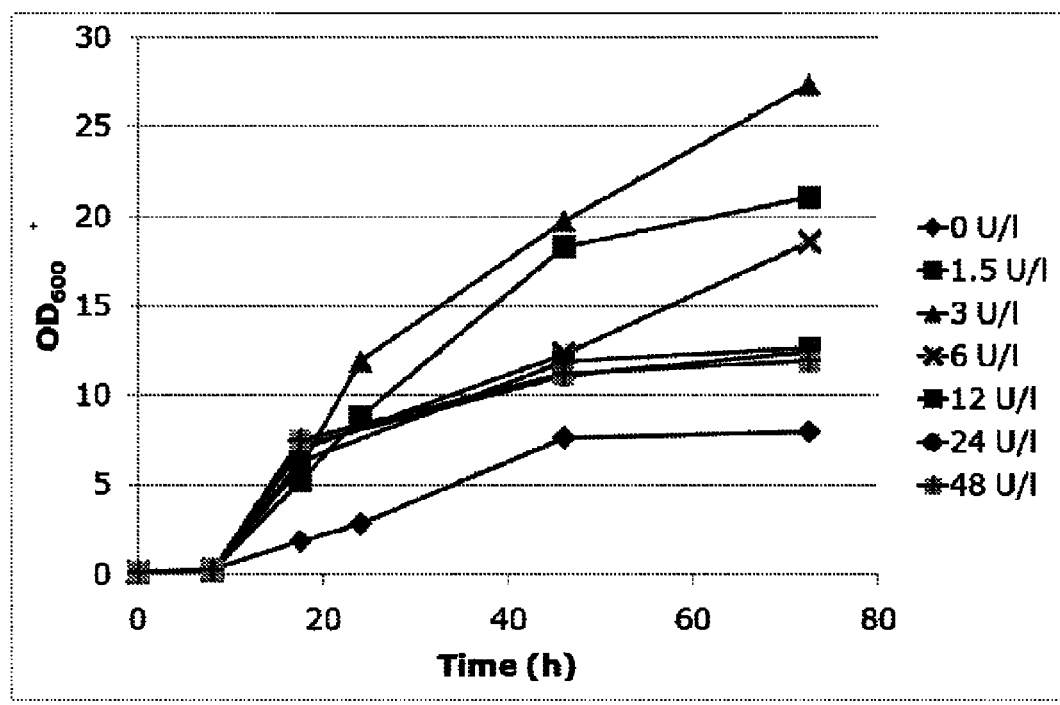
FIG. 2 illustrates graphically the growth of E. coli strain BL21(DE3) in liquid mineral salt medium, containing dextrin as the substrate-polymer and glucoamylase (E.C. 3.2.1.3.) as an added dextrin-degrading enzyme at different concentrations. The growth rate depends on time and the concentration of the enzyme glucoamylase (E.C. 3.2.1.3.).

The growth behavior of *E. coli* BL21(DE3) in a liquid mineral salt medium containing the substrate-polymer dextrin and various amounts of the substrate-polymer degrading enzyme glucoamylase ranging from 0 to 96 U/l was selected for the present study (FIG. 2). The cultivation success was observed to strongly depend on the concentration of the enzyme glucoamylase. Without the addition of glucoamylase, indicated by diamonds (♦), only poor growth was obtained with the maximum cell density ($OD_{600}=7.5$) after 48 h of cultivation. Thus, the cells used tryptone, yeast extract and the small-size glucose-oligomers of dextrin as a carbon and energy source but only with a low efficiency. In contrast to the assumption of Example 1, which proposed the highest cell density with 24 U/l glucoamylase, the highest cell density of $OD_{600}=27.5$ was obtained with 3 U/l glucoamylase, as indicated by a triangle (▲). This suggests that high enzyme doses yield glucose accumulation and production of growth-inhibiting metabolites. Since the cells did not enter the stationary phase after 72 h of cultivation, one can assume that the maximum cell density was not reached. This means that the growth efficiency of the cells was increased compared to the growth with tryptone and yeast extract as carbon and energy source due to the controlled and limited enzymatic release of glucose from the substrate-polymer dextrin. The data also show that lower enzyme concentrations can be applied if one would aim for slow controlled growth. The experiment with 1.5 U/l glucoamylase, indicated by a squares (■), reached a value of $OD_{600}=21$, i.e. a lower cell density than the experiment with 3 U/l glucoamylase. The experiments with 6, 12, 24, 48 or 96 U/l glucoamylase, however, resulted in lower cell density values ranged from $OD_{600}$=12 to 18. Probably, the higher amount of the degrading enzyme causes accumulation of glucose, whereby the cells underwent metabolic phenomena with an oxygen depletion and secretion of large amounts of growth-inhibiting by-products (Luli W. R. & W. R. Strohl, Appl. Environ. Microbiol., 1990, 56:1004-1011; Riesenberg D. et al., J. Biotechnol., 1991, 20:17-28).

Thus, by changing the amount of the polymer-degrading enzyme, one can easily establish the optimal speed of the substrate-monomer release, i.e. an enzyme-based fed-batch technique is provided for laboratory-scale liquid high-cell-density cultivation.

Example 3

Enzyme-Based Fed-Batch Cultivation of *E. coli* in Liquid Mineral Salt Medium Containing Dextrin and the Enzyme Glucoamylase Compared to Batch Cultivation with Terrific Broth (TB)

*E. coli* strain BL21(DE3) cultivation in liquid mineral salt medium containing dextrin as a substrate-polymer was compared to ordinary batch shake flask cultivation with Terrific Broth (TB). Averages of two parallel shake flasks of each cultivation system are presented in FIG. 3.

A liquid mineral salt medium (MSM; Neubauer P. et al., Biotechnol. Bioeng., 1995, 47:139-146) was used as the general base for the cultivation medium, which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4.H_2O$, 1.0 g $(NH_4)_2$—H-citrate. 0.24 g tryptone, 0.48 g yeast extract. For present experiment, 50 g/l soluble dextrin was added as carbon and energy source, i.e. as the substrate-polymer. The components were mixed with 1 liter of distilled water, autoclaved and cooled. Prior to inoculation, the basal medium containing dextrin was supplemented with 3 mM $MgSO_4$, 2 ml/l of trace element solution (Holme T. et al., Process Biochem., 1970, 5:62-66) and 0.1 g/l of thiamine hydrochloride. As a control, flasks with Terrific Broth (TB, Tartof K. D. & Hobbs C. A., Bethesda Res. Lab. Focus, 1987, 9: 19) medium (per liter: 12 g tryptone, 24 g yeast extract, 4 g glycerol, 9.4 g $K_2HPO_4$, 2.2 g $KH_2PO_4$ (pH 7.2)) was prepared. Cultivation experiments were performed using a pure culture of *E. coli* strain BL21(DE3). The precultures were prepared by washing bacteria from freshly-cultivated Luria Bertani (LB)-plates with mineral salt medium (2 ml per plate) containing neither glucose nor dextrin. The plate washout was used as an inoculants to yield initial cell density of $OD_{600}$=0.1 in each shake flask.

For cultivation, 100 ml-aliquots of the dextrin-containing MSM medium or TB medium were distributed into sterile 500 ml Erlenmeyer glass shake flasks. Shake flasks were inoculated with the preculture to $OD_{600}$=0.1. After inoculation, 3.0 U/l of the enzyme glucoamylase from *Aspergillus niger* (E.C. 3.2.1.3.; Amylase AG 300L, Novozymes, Bagsværd, Denmark) was added to the dextrin/MSM shake flasks and the cultivation was immediately started at 37° C. on an orbital shaker (180 rpm). Cell growth was followed with a spectrophotometer after the dilution of culture samples in growth medium with a Victor³ Multiwell Plate Reader (Perkin Elmer, Waltham, USA) at a wavelength of 490 nm. Conversion to $OD_{600}$ values was made according to a standard curve. One unit of $OD_{600}$ corresponds to a dry cell weight of 0.3 g/l (Soini J. et al., Microb. Cell Fact., 2008, 7:26).

Figure 3:
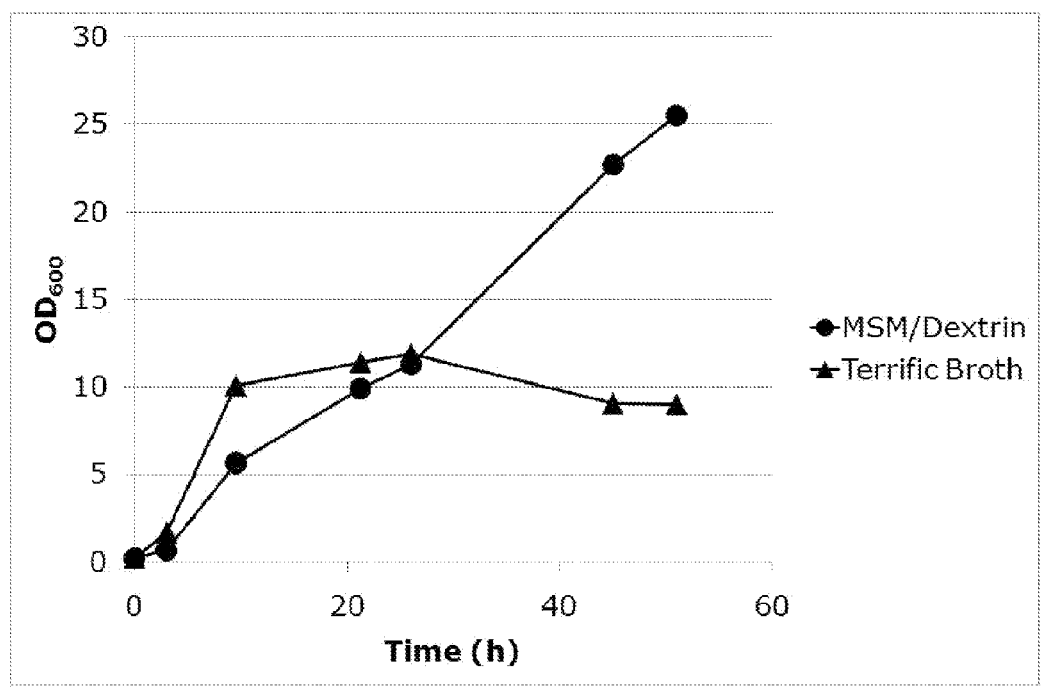
FIG. 3 illustrates graphically how the growth of E. coli BL21(DE3) can be controlled and higher cell densities can be obtained by using enzyme-based glucose release in liquid mineral salt medium containing 40 g/l dextrin with 3 U/l glucoamylase (E.C. 3.2.1.3), as indicated by circles (●). A batch cultivation in Terrific Broth (TB), as indicated by triangles (▲), shows non-controlled growth and yields lower cell densities.

FIG. 3 shows uncontrolled growth of the cells in TB medium with a maximum value of $OD_{600}$ of approximately 12 after 24 h of cultivation ($OD_{600}$ of 10 already after 9 h cultivation) after which the stationary phase begins. Thus, TB medium is not suitable for a controlled growth of microbial prokaryotic or eukaryotic cells. However, liquid mineral salt medium containing dextrin as the substrate-polymer and glucoamylase as the dextrin-degrading enzyme causes exclusively linear growth up to an $OD_{600}$-value of approximately 25 without reaching the stationary phase. Thus, the controlled limited release of glucose offers a possibility for a high cell density in laboratory-scale liquid shaken microbial prokaryotic and eukaryotic cell cultures.

Therefore, the use of liquid mineral salt medium containing dextrin as the growth-limiting substrate and the degrading enzyme glucoamylase results in a higher cell density than the use of TB medium, wherein mainly tryptone, yeast-extract and a low amount of glycerol represent the carbon and energy source.

Example 4

Enzyme-Based Fed-Batch Cultivation of *E. coli* in Liquid Mineral Salt Medium Containing Saccharose and the Enzyme Invertase Effects of different amounts of the enzyme invertase on the growth of *E. coli* strain BL21(DE3) was tested in liquid mineral salt medium containing the substrate-oligomer saccharose. A liquid mineral salt medium (MSM; Neubauer P. et al., Biotechnol. Bioeng., 1995, 47:139-146) was used as the general base for the cultivation medium, which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4.H_2O$, 1.0 g $(NH_4)_2$—H-citrate. For present experiment, 10 g/l saccharose was added as carbon and energy source, i.e. as the substrate-oligomer. The components were mixed with 1 liter of distilled water, autoclaved and cooled. Prior to inoculation, the basal medium was supplemented with 3 mM $MgSO_4$, 2 ml/l of trace element solution (Holme T. et al., Process Biochem., 1970, 5:62-66) and 0.1 g/l of thiamine hydrochloride. The precultures were prepared by washing bacteria from freshly-cultivated Luria Bertani (LB)-plates with mineral salt medium (2 ml per plate). The plate washout was used as an inoculants to yield initial cell density of $OD_{600}$=0.1 in each cultivation well.

For cultivation, 1.5 ml-aliquots of the MSM medium containing saccharose were distributed into sterile 48-deepwell-plates (Ritter, Germany) having a total volume of 1.5 ml. The respective amounts of invertase, i.e. 0, 0.1, 0.5, 1, 5, 10 or 100 U/l, were added after inoculation and the culture was immediately started at 37° C. on an orbital shaker (180 rpm). In addition, the amount of 1000 U/l invertase was used when testing the growth of *E. coli* in the medium. Cell growth was followed after 18 and 24 h of incubation with a spectrophotometer after the dilution of culture samples in growth medium with a Victor³ Multiwell Plate Reader (Perkin Elmer, Waltham, USA) at a wavelength of 490 nm. Conversion to $OD_{600}$ values was made according to a standard curve. One unit of $OD_{600}$ corresponds to a dry cell weight of 0.3 g/l (Soini J. et al., Microb. Cell Fact., 2008, 7:26). The glucose analysis was performed after 2.5 and 19 h of incubation with YSI 2700 Select Biochemical Analyzer (YSI Inc., Yellow Springs, USA).

Figure 4A:
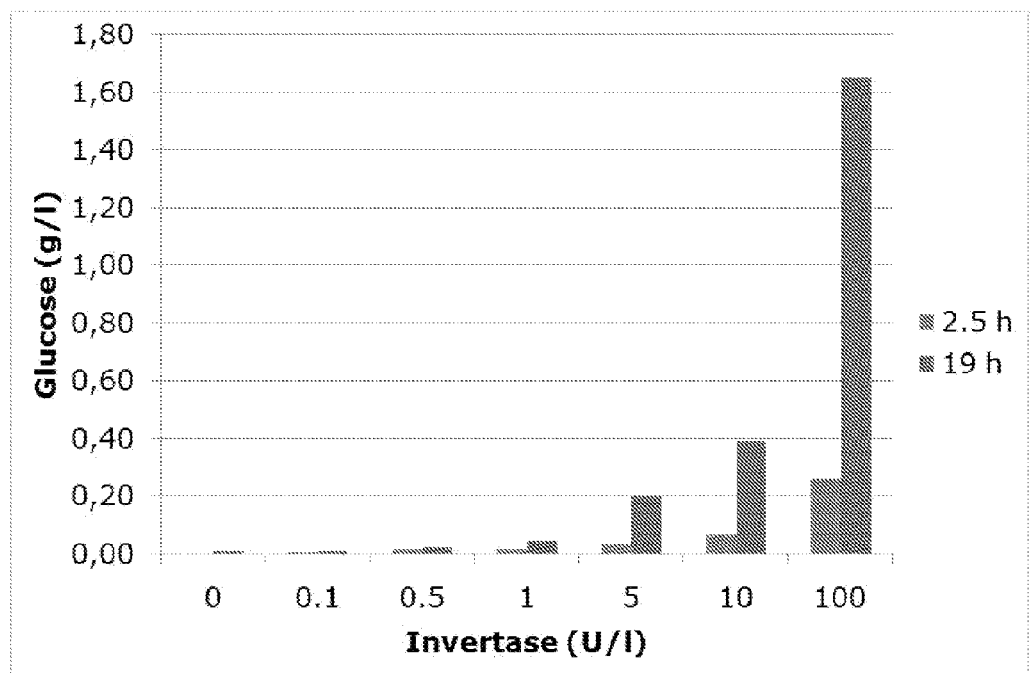
FIG. 4a illustrates graphically the release rate of the growth-limiting substrate-monomer glucose from the disaccharide saccharose (sucrose) using different concentrations of the saccharose-degrading enzyme invertase (E.C. 3.2.1.26)
Figure 4B:
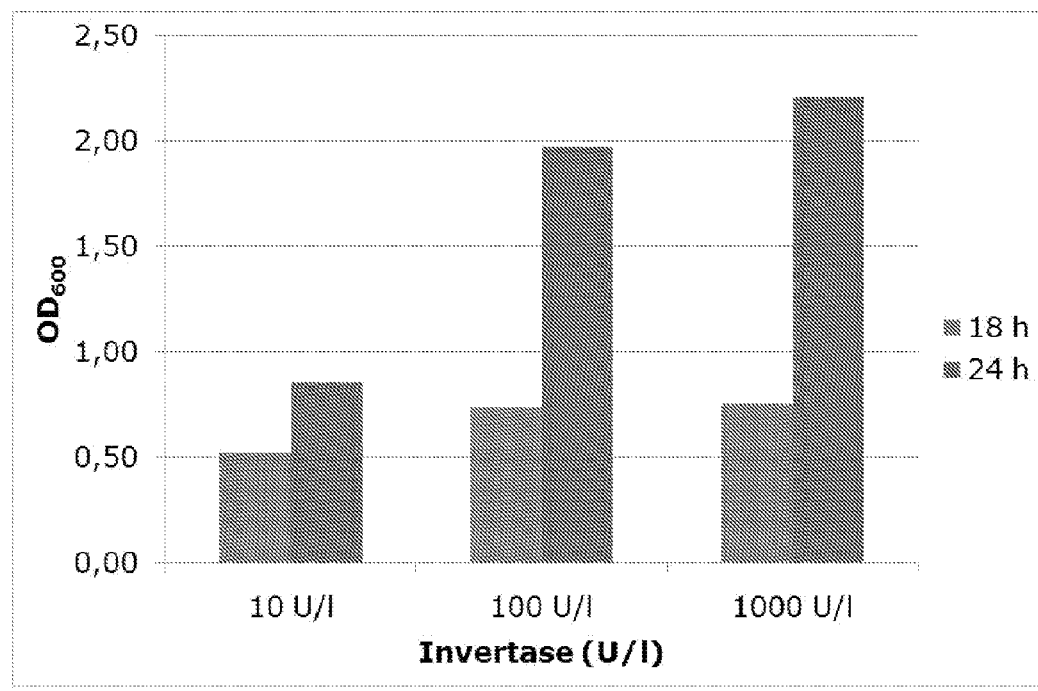
FIG. 4b illustrates graphically the growth of E. coli BL21 (DE3) in liquid mineral salt medium containing saccharose as the substrate-polymer and invertase (E.C. 3.2.1.26) as an added saccharose-degrading enzyme at different concentrations.

The growth behavior of *E. coli* strain BL21(DE3) in a liquid mineral salt medium containing the disaccharide saccharose and various amounts of the substrate-polymer degrading enzyme invertase ranging from 0 1000 U/l was selected for the present study (FIGS. 4a and b). The glucose release rate was dependent on the tested range of enzyme concentration (FIG. 4a). Without the addition of invertase, no glucose release was observed, whereas 100 U/l glucoamylase gave the highest glucose release rate of approximately 1.65 g/l at the maximum after 19 h of incubation. The glucose release value obtained with 100 U/l of invertase was 4.2 fold higher than the glucose release value obtained with 10 U/l. Thus, for fed-batch type cultivation experiments with *E. coli* an invertase amount of 100 U/1 may be proposed as a good starting point. Also the cultivation success was observed to strongly depend on the concentration of the enzyme invertase (FIG. 4b). After 18 h of incubation, the $OD_{600}$-values for the samples with 10, 100 and 1000 U/l of the enzyme invertase were pretty similar, ranging from approximately $OD_{600}$=0.5 to $OD_{600}$=0.7. Bigger differences in cell densities were obtained after 24 h of incubation, where 1000 U/l results in the highest cell density showing an $OD_{600}$-value of approximately 2.2. This value, however, was only slightly higher than the value obtained with 100 U/l showing an $OD_{600}$-value of approximately 2.0. Probably, the higher enzyme concentration (1000 U/l) leads to a higher metabolically active substrate concentration, i.e. the concentration of released glucose and fructose, which causes that the cells underwent unfavorable metabolic resulting in secretion of growth-inhibiting by-products (Luli W. R. & W. R. Strohl, Appl. Environ. Microbiol., 1990, 56:1004-1011; Riesenberg D. et al., J. Biotechnol., 1991, 20:17-28).

Thus, by changing the amount of the polymer-degrading enzyme, one can easily establish the optimal speed of the substrate-monomer release, i.e. an enzyme-based fed-batch technique is provided for a controlled high-cell-density cultivation.

Example 5

Enzyme-Based Glucose-Feeding for Recombinant Protein Production

The *E. coli* strain BL21(DE3)-851 carrying plasmid pET21 containing a gene encoding a 15 kDa A-domain of human protein disulfide isomerase (PDI, E.C. 5.3.4.1.) was cultivated for recombinant PDI production in two different media. Flask 1 (1-liter-flask filled with 100 ml medium) contained a liquid mineral salt medium (MSM; Neubauer P. et al., Biotechnol. Bioeng., 1995, 47:139-146) as the general base for the cultivation medium, which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4.H_2O$, 1.0 g $(NH_4)_2$—H-citrate. The medium was further supplemented with 0.24 g tryptone and 0.48 g yeast extract. For present experiment, 40 g/l soluble dextrin was added as carbon and energy source, i.e. as the substrate-polymer. The components were mixed with 1 liter of distilled water, autoclaved and cooled. Prior to inoculation, the basal medium containing dextrin was supplemented with 3 mM $MgSO_4$, 2 ml/l of trace element solution (Holme T. et al., Process Biochem., 1970, 5:62-66) and 0.1 g/l of thiamine hydrochloride. Flask 2 (5-liter-flask filled with 500 ml medium) contained Luria Bertani (LB)-medium.

Cultivation experiments were performed using a pure culture of *E. coli* strain BL21 (DE3)-851. The precultures were prepared by washing bacteria from freshly-cultivated LB-plates with liquid mineral salt medium (2 ml per plate) containing neither glucose nor dextrin. The plate washout was used as an inoculants to yield initial cell density of $OD_{600}$=0.1 in each cultivation well. Cell growth was followed with a spectrophotometer after the dilution of culture samples in growth medium with a Victor$^3$ Multiwell Plate Reader (Perkin Elmer, Waltham, USA) and a sample volume of 5 µl by measurements of the optical density at a wavelength of 490 nm. Conversion to $OD_{600}$ values was made according to a standard curve. One unit of $OD_{600}$ corresponds to a dry cell weight of 0.3 g/l (Soini J. et al., Microb. Cell Fact., 2008, 7:26).

Flask 1 (referred as EnBase flask in FIG. 5) was inoculated with the preculture of *E. coli* strain BL21 (DE3)-851 to cell density of $OD_{600}$=0.1 and 1.5 U/l glucoamylase was added. Bacteria were cultivated overnight at 37° C. with 200 rpm shaking resulting in a cell density of $OD_{600}$=5.1 after 18 h incubation. Induction was then performed with 1 mM IPTG. At the time of induction, an extra dose of glucoamylase (3 U/l), 1.2 g/l tryptone and 2.4 g/l of yeast extract were added. After 3.5 h induction at 37° C. with 200 rpm shaking the cells were collected. Flask 2 was inoculated with the preculture of *E. coli* strain BL21 (DE3)-851 to cell density of $OD_{600}$=0.1 in 500 ml culture volume of Luria-Bertani (LB) medium in a 5-liter-shake-flask and cultivated at 37° C. with 200 rpm shaking until $OD_{600}$ reached 0.5. The culture was then induced with 1 mM IPTG for 3.5 hours at 37° C. with 200 rpm shaking.

After induction samples were taken: from Flask 1 volume samples of 20 ml and 80 ml volume and from Flask 2 samples of 100 ml and 300 ml volume. Bacteria were harvested by centrifugation and suspended to 5 ml of sample buffer (50 mM sodium phosphate pH 7.0, 0.2 M NaCl). For SDS-PAGE analysis 0.2 ml samples were taken, and the cells were disrupted by sonication (MSE Soniprep, 10 passages of 10 second). Thereafter the samples, which were analyzed for soluble protein were centrifuged (5 min 10000×g) to remove the insoluble protein fraction. Samples were analyzed by SDS-PAGE protocol (12% separating gels) by using standard protocols.

Figure 5:
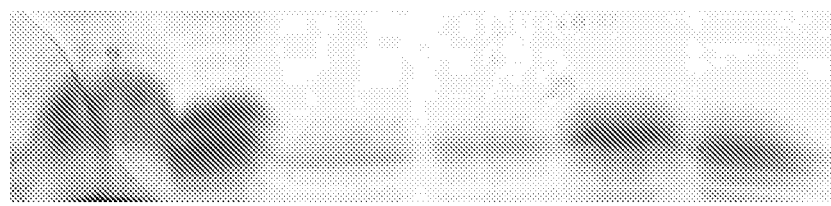
FIG. 5 shows that an improved production of recombinant protein (human protein disulfide isomerase A-domain, 15 kDa in size) can be achieved by the enzyme-based fed-batch technique compared to a standard induction protocol using Luria Bertani (LB) medium.

As seen in FIG. 5, considerably higher production of PDI per volume was achieved by liquid enzyme-based fed-batch cultivation (referred as EnBase). The productivity per biomass was about the same (not shown) in both cultivations, but since 10-fold higher induction cell density can be used with the liquid enzyme-based fed-batch technique, also 5 to 10-fold higher protein yields per volume was obtained. The possibility to maintain favorable culture conditions longer may further facilitate longer induction times and much higher biomass and protein yields with enzyme-based fed-batch cultivation.

Example 6

Methods for Quick Medium Preparations

1. Liquid ready-made sterile mineral salt medium containing a substrate-Polymer, E.G. Dextrin as a Glucose Source:

Liquid ready-made sterile medium for controlled high-cell-density cultivation containing e.g. dextrin as a glucose source is performed by mixing the components of a liquid mineral salt medium (MSM; Neubauer P. et al., Biotechnol. Bioeng., 1995, 47:139-146), which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4.H_2O$, 1.0 g $(NH_4)_2$—H-citrate. Also 0.24 g tryptone, 0.48 g yeast extract, and 50 g/l soluble dextrin as substrate-polymer were added per 1 liter. Medium was sterilized by autoclaving and cooled.

Prior to inoculation of e.g. *E. coli* strain BL21(DE3), the basal medium containing e.g. dextrin has to be supplemented with 3 mM $MgSO_4$, 2 ml/l of trace element solution (Holme T. et al., Process Biochem., 1970, 5:62-66) and 0.1 g/l of thiamine hydrochloride. After inoculation, a substrate-polymer degrading enzyme has to be added, e.g. 3.0 U/l of the enzyme glucoamylase from *Aspergillus niger* (E.C. 3.2.1.3.;

Amylase AG 300L, Novozymes, Bagsværd, Denmark) and the cultivation has to be started immediately.

2. Pre-sterilized liquid mineral salt medium powder containing a substrate-Polymer, E.G. Dextrin as a Glucose Source:

The components of the liquid mineral salt medium recipe as described above containing e.g. 50 g/l soluble dextrin as growth-limiting substrate-polymer (per liter), were used to prepare a well-mixed powder, which is divided into plastic packages (each yielding a 100 ml portion of ready medium) and sterilized by irradiation. The powder can be distributed in sterile shake flasks and used for quick medium preparation. Therefore, the powder is mixed with 100 ml of sterile distilled water and dissolved by heating in a microwave oven (700 watt) for 1 min or, alternatively, the medium can be autoclaved for dissolving.

Prior to inoculation of e.g. *E. coli* strain BL21(DE3), the basal medium containing e.g. dextrin has to be supplemented with 3 mM $MgSO_4$, 2 ml/l of trace element solution (Holme T. et al., Process Biochem., 1970, 5:62-66) and 0.1 g/l of thiamine hydrochloride. After inoculation, a substrate-polymer degrading enzyme has to be added, e.g. 3.0 U/l of the enzyme glucoamylase from *Aspergillus niger* (E.C. 3.2.1.3.; Amylase AG 300L, Novozymes, Bagsværd, Denmark) and the cultivation has to be started immediately.

3. Pre-Sterilized Mineral Salt Medium Tablets Containing a Substrate-Polymer, E.G. Dextrin as Substrate-Polymer for Quick Medium Preparation:

The components of a liquid mineral salt medium recipe (MSM) as described above containing e.g. 50 g/l soluble dextrin as growth-limiting substrate-polymer (per liter), were used to prepare tablets sufficient for 50 ml cultures. To the chemical mixture measured for one liter medium, 30 ml of 70% ethanol was added to obtain a thick slurry, which is suitable for tablet manufacturing. The mixture was divided into 20 portions, and tablets with a diameter of 22 mm and thickness of about 25 mm were prepared with a hydraulic press. These tablets (preferably sterilized by irradiation) were used for fast medium preparation by adding water (50 ml per one tablet) and dissolving the tablet by heating (700 watt) 1 min in a microwave oven.

Prior to inoculation of e.g. *E. coli* strain BL21(DE3), the basal medium containing e.g. dextrin has to be supplemented with 3 mM $MgSO_4$, 2 ml/l of trace element solution (Holme T. et al., Process Biochem., 1970, 5:62-66) and 0.1 g/l of thiamine hydrochloride. After inoculation, a substrate-polymer degrading enzyme has to be added, e.g. 3.0 U/l of the enzyme glucoamylase from *Aspergillus niger* (E.C. 3.2.1.3.; Amylase AG 300L, Novozymes, Bagsværd, Denmark) and the cultivation has to be started immediately.

Example 7

Preparation of Cultivation Vessels with Pre-Filled or Coated Mineral Salt Medium Containing a Substrate-Polymer, E.G. Dextrin A ten-fold concentration of a liquid mineral salt medium (e.g. MSM; Neubauer P. et al., Biotechnol. Bioeng., 1995, 47:139-146) was prepared, which comprises (per liter): 20 g $Na_2SO_4$, 27 g $(NH_4)_2SO_4$, 5 g $NH_4Cl$, 146 g $K_2HPO_4$, 36 g $NaH_2PO_4.H_2O$, 10 g $(NH_4)_2$—H-citrate. In addition, 2.4 g tryptone and 4.8 g yeast extract was added. Also, a 2.5-fold concentrate (100 g/l) of soluble dextrin as a substrate-polymer was prepared. These components were sterilized by autoclaving, cooled and combined in the following relationship: 1 liter of 10-fold medium concentrate and 4 liters of 2.5-fold soluble dextrin. The resulting 2-fold concentrate of MSM/Dextrin mixture was distributed into cultivation vessels, e.g. 75 µl per sample well into microtiter plates, which have a total volume of 200 µl. The pre-filled microtiter plates can be either directly packed and sterilized by irradiation or the liquid can be first dried at 37° C. leaving sample wells coated with a layer of the cultivation medium. In the case of dried medium, the solid layer of cultivation medium can be dissolved by the addition of sterile distilled water, e.g. 150 µl of water and used for liquid cultures of microbial prokaryotic or eukaryotic cells.

Prior to inoculation of e.g. *E. coli* strain BL21(DE3), the basal medium containing e.g. dextrin has to be supplemented with 3 mM $MgSO_4$, 2 ml/l of trace element solution (Holme T. et al., Process Biochem., 1970, 5:62-66) and 0.1 g/l of thiamine hydrochloride. After inoculation, a substrate-polymer degrading enzyme has to be added, e.g. 3.0 U/l of the enzyme glucoamylase from *Aspergillus niger* (E.C. 3.2.1.3.; Amylase AG 300L, Novozymes, Bagsværd, Denmark) and the cultivation has to be started immediately.

Example 8

Examples of Cultivation Vessels that can be Used with the Described Innovation

A liquid mineral salt medium containing a substrate-polymer and a substrate-polymer degrading enzyme can be used as the general base cultivation medium for the enzyme-based fed-batch technique in bioreactors ranging from microbioreactors to several cubic meters reactors.

A liquid mineral salt medium (e.g. MSM; Neubauer P. et al., Biotechnol. Bioeng., 1995, 47:139-146), which comprises (per liter): 2 g $Na_2SO_4$, 2.7 g $(NH_4)_2SO_4$, 0.5 g $NH_4Cl$, 14.6 g $K_2HPO_4$, 3.6 g $NaH_2PO_4.H_2O$, 1.0 g $(NH_4)_2$—H-citrate, was used as the general base for the cultivation medium. 0.24 g tryptone, 0.48 g yeast extract, and e.g. 50 g/l soluble dextrin as the growth-limiting substrate-polymer were added to the medium. The components (basic medium and dextrin) can also be prepared and sterilized as separate (at least 2-fold) concentrates and then combined. Prior to inoculation, the liquid basal medium containing dextrin was supplemented with 3 mM $MgSO_4$, 2 ml/l of trace element solution (Holme T. et al., Process Biochem., 1970, 5:62-66) and 0.1 g/l of thiamine hydrochloride.

Example 8a

Use of the Enzyme-Based Fed-Batch Technique in a Microbioreactor with a Total Volume of 200 µl Cultivation experiments were performed using a pure culture of *E. coli* strain BL21(DE3) and the liquid mineral salt medium as described above. Precultures of *E. coli* strain BL21(DE3) were prepared from frozen glycerol-stocks plated on agar-solidified MSM-glucose medium by overnight cultivation of the strain at 37° C. For inoculation, one colony of *E. coli* strain BL21(DE3) per each sample plate was picked with a sterile micropipette tip and transferred to the cultivation well.

For cultivation, 150 µl-aliquots of the liquid mineral salt medium containing dextrin were distributed into 96-well microtiter plates (Perkin Elmer Spectra Plate™-96 TC, Waltham, USA), whereas each well has a total volume of 200 µl. After inoculation, 3.0 U/l of the enzyme glucoamylase from *Aspergillus niger* (E.C. 3.2.1.3.; Amylase AG 300L, Novozymes, Bagsværd, Denmark) was added and the culture was immediately started at 30° C. in an Variomag Thermoshaker (with TEC-controller 485, Inheco, Munich, Germany) at 1000 rpm. Cell growth was followed with a spectrophotometer after the dilution of culture samples in growth medium with a Victor$^3$ Multiwell Plate Reader (Perkin Elmer, Waltham, USA) at a wavelength of 490 nm. Conversion to $OD_{600}$ values was made according to a standard curve. One unit of $OD_{600}$ corresponds to a dry cell weight of 0.3 g/l (Soini J. et al., Microb. Cell Fact., 2008, 7:26).

After overnight shaking, cell densities of more than $OD_{600}=10$ were typically observed. After 48 h shaking, $OD_{600}=30$ were normally detected. Thus, present enzyme-based fed-batch technique can be used for small volumes, e.g. a microbioreactor with a volume of 200 µl.

Example 8b

Use of the Quick Medium-Preparation Tablets for Enzyme Based Fed-Batch Cultivation in a Shake Flask with a Total Volume of 1000 ml For the cultivation experiment, the dry components of the liquid mineral salt medium recipe containing 50 g/l soluble dextrin were used for the preparation of tablets sufficient for 100 ml cultures. To the chemical mixture measured for one liter medium, 30 ml of 70% ethanol was added to obtain a thick slurry suitable for tablet manufacturing. The mixture was divided into 10 portions, and tablets with a diameter of 22 mm and thickness of about 25 mm were prepared with a hydraulic press. These tablets were used for fast medium preparation by adding water (100 ml per one tablet) and dissolving the tablet by heating (700 watt) 2 min in a microwave oven. Cultivation experiments were performed using a pure culture of *E. coli* strain BL21(DE3). The precultures were prepared by washing bacteria from freshly-cultivated LB-plates with liquid mineral salt medium (2 ml per plate) containing neither glucose nor dextrin. The plate washout was used as an inoculant to yield initial cell density of $OD_{600}=0.1$.

For cultivation, liquid mineral salt medium tablets, as described above, were distributed into 1000 ml Erlenmeyer shake flasks and supplemented with 100 ml of sterile distilled water. The shake flask was heated for 2 min in a microwave oven (700 watt) to fully dissolve the media components of the tablet into the water. Growth experiments were inoculated with washed preculture cell suspensions to a final cell concentration of $OD_{600}=0.1$. After inoculation, 3.0 U/l of the enzyme glucoamylase from *Aspergillus niger* (E.C. 3.2.1.3.; Amylase AG 300L, Novozymes, Bagsværd, Denmark) was added and the culture was immediately started at 37° C. on an orbital shaker with an amplitude of 5 cm and 200 rpm). Cell growth was followed with a spectrophotometer after the dilution of culture samples in growth medium with a Victor$^3$ Multiwell Plate Reader (Perkin Elmer, Waltham, USA) at 490 nm wavelengths. Conversion to $OD_{600}$ values was made according to a standard curve. One unit of $OD_{600}$ corresponds to a dry cell weight of 0.3 g/l (Soini J. et al., Microb. Cell Fact., 2008, 7:26).

Pre-sterilized mineral salt medium tablets containing a substrate-polymer, e.g. dextrin as substrate-polymer can be used for the present enzyme-based fed-batch technique in shake flasks. To evaluate the applicability of the tablet-based medium for bacterial cultivation, parallel medium bottles were prepared by a) using medium made from concentrated liquids as described in example 3, and b) by preparing medium from pre-sterilized tablets as described above. Cultivations of *E. coli* BL21 (DE3) in a 100 ml culture volume, with initial $OD_{600}=0.1$ and with 3 U/l glucoamylase dose showed similar growth characteristics between these bottles during 48 h cultivation (results not shown).

Example 8c

Use of the Fed-Batch Slow-Release Technique in a Bioreactor with a Total Volume of 6 Liters Cultivation experiments were performed with *E. coli* strain BL21(DE3) and the liquid mineral salt medium containing 50 g/l soluble dextrin as described above.

The precultures of *E. coli* strain BL21 (DE3) were prepared in Luria Bertani (LB) medium, which comprises (per liter): 5.0 g yeast extract, 10.0 g caseine peptone, 10.0 g NaCl. Preculture *E. coli* strain BL21 (DE3) was prepared from frozen glycerol-stocks in 100 ml Erlenmeyer flasks containing 10 ml of LB medium by overnight cultivation of the strain at 37° C. on an orbital shaker (180 rpm). For inoculation, the preculture medium was removed by centrifugation (23° C., 3200×g, 20 min) and the pellet was resuspended in dextrin-free liquid mineral salt medium.

For cultivation, 6 liter of the liquid mineral salt medium containing dextrin was distributed into a very simple sterile bioreactor, which is equipped only with heating and mixing possibilities and not with control (liquid feeding) possibilities, e.g. Braun BIOSTAT® C bioreactor (B. Braun Biotech International GmbH, Melsungen, Germany). The cultivation medium was inoculated with a washed preculture cell suspension of *E. coli* strain BL21(DE3) to a final cell concentration of $OD_{600}=0.1$. After inoculation, 6 U/l of the enzyme glucoamylase from *Aspergillus niger* (E.C. 3.2.1.3.; Amylase AG 300L, Novozymes, Bagsværd, Denmark) was added and the culture was immediately started at 37° C., with a mixing of 200 rpm and an airflow of 4 l/min. During the fermentation the dissolved oxygen level (DOT) was maintained at a level of above 30% by stepwise increasing the stirrer speed and the airflow, whereas no pH control was used. Cell growth was followed with a spectrophotometer after the dilution of culture samples in growth medium with a Victor$^3$ Multiwell Plate Reader (Perkin Elmer, Waltham, USA) and a sample volume of 5 µl by measurements of the optical density at a wavelength of 490 nm. The corresponding $OD_{600}$-values were calculated according to a standard curve. One unit of $OD_{600}$ corresponds to a dry cell weight of 0.3 g/l (Soini J. et al., Microb. Cell Fact., 2008, 7:26). An oxygen electrode was used to register the dissolved oxygen level (DOT).

Cell growth with a maximum value of $OD_{600}=40$ was achieved within 24 hours. Thus, present enzyme-based fed-batch technique can be used for large volumes, e.g. a bioreactor with a total volume of 6 liters.

The invention claimed is:

1. A method for controlling, in a cultivation of at least one of microbial prokaryotic cells or microbial eukaryotic cells, the growth of said cells in a single-phase, liquid culture medium to high cell densities by an enzyme-based fed-batch technique, wherein a metabolically inactive water soluble substrate-polymer or substrate-oligomer is degraded by the controlled addition of an enzyme to release the growth-limiting substrate-monomer in a controlled way into the single-phase, liquid culture medium, wherein if the cells grow slowly and the oxygen level in the culture medium stays high more enzyme is added and if the oxygen content in the culture medium becomes so low that anaerobic conditions occur no further enzyme is added, wherein the substrate-polymer or substrate-oligomer is present in an amount of 10 to 50 g/l.

2. The method of claim 1, wherein the substrate-polymer or substrate-oligomer cannot be directly degraded by the microbial prokaryotic or eukaryotic cells.

3. The method of claim 1, wherein the substrate-oligomer or substrate-polymer is added either at the beginning of cultivation or during cultivation in one or several batches or by continuous feed.

4. The method claim 1, wherein the substrate-polymer or substrate-oligomer is a glucose-polymer or glucose-oligomer, selected from the group consisting of cellulose ($\beta$-1,4-glucan), curdlan ($\beta$-1,3-glucan), dextran ($\alpha$-1,6-glucan), glycogen ($\alpha$-1,4- and $\alpha$-1,6-glucan), laminarin ($\beta$-1,3- and $\beta$-1,6-glucan), lentinan ($\beta$-1,6:$\beta$-1,3-glucan), lichenin, pleuran ($\beta$-1,3- and $\beta$-1,6-glucan), pullulan ($\alpha$-1,4- and $\alpha$-1,6-glucan), starch ($\alpha$-1,4- and $\alpha$-1,6-glucan), and zymosan ($\beta$-1,3-glucan).

5. The method of claim 1, wherein the substrate-polymer or substrate-oligomer is selected from the group consisting of soluble-starch derivatives and dextrin.

6. The method of claim 1, wherein the enzyme is selected from the group consisting of amylases, proteases, peptidases, nucleases and amidases.

7. The method of claim 3, wherein the substrate-polymer or substrate-oligomer is present in an amount of 20 to 50 g/l.

8. The method of claim 1, wherein the liquid phase medium contains complex additives selected from the group consisting of peptones, casamino acids, and yeast extract.

9. The method of claim 1, wherein the liquid phase medium further comprises (a) at least one mineral salt medium, (b) at least one of microbial prokaryotic cells and microbial eukaryotic cells, (c) at least one of the substrate-polymer and the substrate-oligomer, and optionally at least one of yeast extract, and tryptone.

10. The method of claim 1, wherein the microbial prokaryotic or eukaryotic cells comprise at least one of bacteria, archaea, protists, fungi, microscopic plants and mammalian suspension cell cultures.

11. The method of claim 1, wherein the cultivation is performed in small-scale or laboratory-scale as shaken cultures or in bioreactors.

12. The method of claim 1, wherein the cultivation is performed in large-scale as shaken cultures or bioreactor cultures.

13. The method of claim 1, wherein the cultivation of the microbe or eukaryotic cell is in carried out in a plastic bag.

14. The method of claim 2, wherein the substrate-oligomer or substrate-polymer is added either at the beginning of cultivation or during cultivation in one or several batches or by continuous feed.

15. The method claim 2, wherein the substrate-polymer or substrate-oligomer is a glucose-polymer or glucose-oligomer, selected from the group consisting of cellulose ($\beta$-1,4-glucan), curdlan ($\beta$-1,3-glucan), dextran ($\alpha$-1,6-glucan), glycogen ($\alpha$-1,4- and $\alpha$-1,6-glucan), laminarin ($\beta$-1,3- and $\beta$-1,6-glucan), lentinan ($\beta$-1,6:$\beta$-1,3-glucan), lichenin, pleuran ($\beta$-1,3- and $\beta$-1,6-glucan), pullulan ($\alpha$-1,4- and $\alpha$-1,6-glucan), starch ($\alpha$-1,4- and $\alpha$-1,6-glucan), and zymosan ($\beta$-1,3-glucan).

16. The method of claim 2, wherein the substrate-polymer or substrate-oligomer is a selected from the group consisting of soluble-starch derivatives and dextrin.

17. The method of claim 2, wherein the substrate-polymer or substrate-oligomer is selected from the group consisting of a cellulose derivative, methylcellulose and carboxymethylcellulose.

18. The method of claim 2, wherein the enzyme is selected from the group consisting of amylases, proteases, peptidases, nucleases and amidases.

19. The method of claim 1, wherein the dissolved oxygen level of the medium is maintained at above 30%.

20. A method for the cultivation of at least one of microbial prokaryotic cells and microbial eukaryotic cells, the method comprising:

culturing the at least one of microbial prokaryotic cells and microbial eukaryotic cells in a single-phase, liquid culture medium that comprises a dissolved metabolically inactive water soluble substrate-polymer or substrate-oligomer; and adding an enzyme to the culture medium in periodic controlled additions during culturing, wherein the enzyme degrades the dissolved metabolically inactive water soluble substrate-polymer or substrate-oligomer and thereby releases a growth-limiting substrate-monomer into the culture medium, and wherein an amount of enzyme added in each of said periodic controlled additions is selected based upon an oxygen content of the culture medium.

* * * * *